(12) United States Patent
Malherbe et al.

(10) Patent No.: US 7,396,853 B2
(45) Date of Patent: Jul. 8, 2008

(54) 2-PHENYL-3,3,3-TRIFLUORO-2-HYDROXY-PROPIONIC ACID DERIVATIVES

(75) Inventors: Parichehr Malherbe, Muttenz (CH); Raffaello Masciadri, Basel (CH); Roger David Norcross, Olsberg (CH); Eric Prinssen, Guebwiller (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 44 days.

(21) Appl. No.: 11/492,462

(22) Filed: Jul. 25, 2006

(65) Prior Publication Data

US 2007/0027204 A1 Feb. 1, 2007

(30) Foreign Application Priority Data

Jul. 28, 2005 (EP) .................. 05106979

(51) Int. Cl.
*A61K 31/404* (2006.01)
*C07D 209/38* (2006.01)

(52) U.S. Cl. ...................... 514/418; 548/485

(58) Field of Classification Search ............. 514/418, 514/470, 544, 570; 548/485; 549/466; 560/105; 562/470
See application file for complete search history.

(56) References Cited

FOREIGN PATENT DOCUMENTS

| EP | 0 825 193 A2 | 2/1998 |
|---|---|---|
| WO | WO 01/56990 | 8/2001 |
| WO | WO 2002/083133 A1 | 10/2002 |
| WO | WO 2005/026208 A2 | 3/2005 |

OTHER PUBLICATIONS

S.J.Enna, Expert Opinion on Investigational Drugs, vol. 6, No. 10, 1997, pp. 1319-1325, XP002399755.
K.Hirota, et al., Toxicology Letters, vol. 100-101, 1998, pp. 203-207, XP002403333.
Hill et al., Nature, 290, pp. 149-152, (1981).
Billinton et al. Trends in Neurosci., 24, 277-282, (2001).
Bowery et al., Pharmacol. Rev.. 54, pp. 247-264, (2002).
Vacher et al., Curr. Drug Targets, CNS Neurol. Disord. 2, pp. 248-259, (2003).
Bettler et al., Physiol Rev. 84, pp. 835-867, (2004).
Kaupmann et al., Nature, 386, pp. 239-246, (1997).
Kaupmann et al., Nature, 396, pp. 683-687, (1998).
Pin et al., Pharmaco.. Ther. 98, pp. 325-354, (2003).
Galvez et al., J. Biol. Chem., 275, pp. 41166-41174, (2000).
Havlickova et al., Mol. Pharmacol. 62, pp. 343-350, (2002).
Kniazeff et al.,J. Neurosci., 22, pp. 7352-7361, (2002).
Schuler et al., Neuron, 31, pp. 47-58, (2001).
Peters et al., Neurogenetics, 2, pp. 47-54, (1998).
Gassmann et al., J Neurosci. 24, pp. 6086-6097, (2004).
Misgeld et al., Prog. Neurobiol. 46, pp. 423-462, (1995).
Enna et al., Life Sci, 62, pp. 1525-1530, (1998).
McCarson et al., Neuropharmacology, 38, pp. 1767-1773, (1999).
Brebner et al., Neuropharmacology, 38, pp. 1797-1804, (1999).
Paterson et al., Psychopharmacology, 172, pp. 179-186, (2004).
Breslow et al., Am. J. Psychiatry, 146, pp. 353-356, (1989).
Drake et al., Ann. Pharmacother. 37., pp. 1177-1181, (2003).
Bortolato et al., Psychopharmacology, 171, pp. 322-330, (2004).
Urwyler et al., Mol. Pharmacol., 60, pp. 963-971, (2001).
Pin et al., Mol. Pharmacol.,60, pp. 881-884, (2001).
Binet et al., J Biol Chem., 279, pp. 29085-29081, (2004).
Urwyler et al., J. Pharmacol. Exp. Ther., 307, pp. 322-330, (2003).
Cryan et al., J Pharmacol Exp Ther., 310, pp. 952-963, (2004).
Smith et al., Psychopharmacology, 173, pp. 105-111, (2004).
Knoflach et al., Proc. Natl. Acad. Sci., USA, 98, pp. 13402-13407, (2001).
Wichmann et al., II Farmaco, 57, pp. 989-992, (2002).
Hammerland et al., Mol. Pharmacol., 53, pp. 1083-1088, (1998).
O'Brien et al., J. Pharmaco. Exp. Ther., 309, pp. 568-577 (2004).
Schaffhauser et al., Mol. Pharmacol., 64, pp. 798-810, (2003).
Dyacheno et al., 1989, vol. 4, pp. 923-928 (Translation).
Calver et al., Neuroscience, vol. 100 pp. 155-170 (2000).
Schwarz et al., J. Biol. Chem. vol. 275, pp. 32174-32181 (2000).
Schwarz et al., J. Biol. Chem. vol. 276, Additions and Corrections, p. 9582 (2001).
Uezono et al., J. Pharmacol. Sci. vol. 94, pp. 211-213 (2004).
Mombereau et al., Neuroreport, vol. 16, pp. 307-310 (2005).
Zai et al., Eur. Neuropsychopharmacol, vol. 15, pp. 347-352 (2005).
Zai et al., Am. J. Med. Genet B, (Neuropsychiart. Genet) vol. 134, pp. 25-29 (2005).
Paterson et al., Neuropsychopharmacology, vol. 30, pp. 119-128 (2005).
Bolser et al., Br. J. Pharmacol. vol. 113, pp. 1344-1348 (1994).
Dicpinigaitis et al., J. Clin. Pharmacol. vol 38, pp. 364-367 (1998).
Dicpinigaitis et al., Arch. Phys. Med. Rehabil. vol. 81, pp. 921-923 (2000).
Cange et al., Ailment Pharmacol. Ther. vol. 16, pp. 869-873 (2002).
Lehmann et al., Eur. J. Pharmacol. vol. 448 pp. 67-70 (2002).
Pehrson et al., J. Urol. vol. 168, pp. 2700-2705 (2002).
Sanger et al., Auton Autacoid Pharmacol. vol. 22, pp. 147-154 (2002).
Symonds et al., Eur. J. Pharmacol. vol. 470, pp. 95-97 (2003).
Piqueras et al., Br. J. Pharmacol. vol. 142, pp. 1038-1048 (2004).
Carai et al., Eur. J. Pharmacol. vol. 504, pp. 213-216 (2004).
Mombereau et al., Neuropsychopharmacology, vol. 29, pp. 1050-1062 (2004).
Casiraghi et al., J. C. S., Perkin Trans., 1983 pp. 1649-1651.
Nicolaou, J. Am. Chem. Soc. (2004) vol. 126, pp. 12888-12896.
Choudhury-Mukherjee et al., J. Med. Chem. 2003, vol. 46, pp. 2494-2501.
Porter et al., Br. J. Pharmacol. vol. 128, pp. 13-20 (1999).
Bartlett et al., J. Am. Chem. Soc. 1954, vol. 76, pp. 2349-2353.

*Primary Examiner*—Charanjit S Aulakh
(74) *Attorney, Agent, or Firm*—George W. Johnston; Patricia S. Rocha-Tramaloni; Kimberly J. Prior

(57) ABSTRACT

The present invention relates to compounds of formula I:

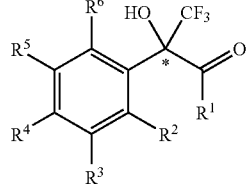

wherein $R^1$, $R^2$, $R^3$, $R^4$, $R^5$ and $R^6$ are as defined in the specification and claims, which compounds are active on the $GABA_B$ receptor and are useful in the control or prevention of CNS illnesses, especially of illnesses and disorders comprising anxiety, depression, epilepsy, schizophrenia, and cognitive disorders.

3 Claims, No Drawings

2-PHENYL-3,3,3-TRIFLUORO-2-HYDROXY-PROPIONIC ACID DERIVATIVES

PRIORITY TO RELATED APPLICATIONS

This application claims the benefit of European Application No. 05106979.7, filed Jul. 28, 2005, which is hereby incorporated by reference in its entirety.

BACKGROUND OF THE INVENTION

γ-Aminobutyric acid (GABA), the most abundant inhibitory neurotransmitter, activates both ionotropic $GABA_{A/C}$ and metabotropic $GABA_B$ receptors (Hill and Bowery, Nature, 290, 149-152, 1981). $GABA_B$ receptors that are present in most regions of the mammalian brain on presynaptic terminals and postsynaptic neurons are involved in the fine-tuning of inhibitory synaptic transmission. Presynaptic $GABA_B$ receptors through modulation of high-voltage activated $Ca^{2+}$ channels (P/Q- and N-type) inhibit the release of many neurotransmitters. Postsynaptic $GABA_B$ receptor activates G-protein coupled inwardly rectifying K+ (GIRK) channel and regulates adenylyl cyclase (Billinton et al., Trends Neurosci., 24, 277-282, 2001; Bowery et al., Pharmacol. Rev. 54, 247-264, 2002). Because the $GABA_B$ receptors are strategically located to modulate the activity of various neurotransmitter systems, $GABA_B$ receptor ligands hence could have potential therapeutics in the treatment of anxiety, depression, epilepsy, schizophrenia and cognitive disorders (Vacher and Bettler, Curr. Drug Target, CNS Neurol. Disord. 2, 248-259, 2003; Bettler et al., Physiol Rev. 84, 835-867, 2004). Moreover, the presence of $GABA_B$ receptors has been confirmed in organs such as spleen, lung, liver, intestine, stomach, esophagus and urinary bladder (Calver et al., Neuroscience, 100, 155-170, 2000; Schwarz et al., J Biol Chem 275, 32174-32181, 2000; Uezono et al., J Pharmacol Sci, 94, 211-213, 2004). Therefore, $GABA_B$ receptor ligands might also have potential therapeutic application in the peripheral nervous system.

Native $GABA_B$ receptors are heteromeric structures composed of two types of subunits, $GABA_BR1$ and $GABA_BR2$ subunits (Kaupmann et al., Nature, 386, 239-246, 1997; Nature, 396, 683-687, 1998). The structures of $GABA_BR1$ and R2 show that they belong to a family of G-protein coupled receptors (GPCRs) called family 3. Other members of the family 3 GPCRs include the metabotropic glutamate (mGlu1-8), calcium-sensing, vomeronasal, pheromone and putative taste receptors (Pin et al., Pharmaco. Ther. 98, 325-354, 2003). The family 3 receptors (including $GABA_B$ receptors) are characterized by two distinctly separated topological domains: an exceptionally long extracellular amino-terminal domain (ATD, 500-600 amino acids), which contains a venus flytrap module for the agonist binding (orthosteric site) (Galvez et al., J. Biol. Chem., 275, 41166-41174, 2000) and the 7TM helical segments plus intracellular carboxyl-terminal domain that is involved in receptor activation and G-protein coupling. The mechanism of receptor activation by agonist in $GABA_BR1R2$ heterodimer is unique among the GPCRs. In the heteromer, only $GABA_BR1$ subunit binds to GABA, while the $GABA_BR2$ is responsible for coupling and activation of G-protein (Havlickova et al., Mol. Pharmacol. 62, 343-350, 2002; Kniazeff et al., J. Neurosci., 22, 7352-7361, 2002).

Schuler et al., Neuron, 31, 47-58, 2001 have demonstrated that the $GABA_BR1$ knock-out (KO) mice exhibit spontaneous seizures and hyperalgesia. These KO mice have lost all the biochemical and electrophysiological $GABA_B$ responses. Interestingly, the $GABA_BR1$ KO mice were more anxious in two anxiety paradigm, namely the light-dark box (decreased time in light) and staircase tests (decreased rears and steps climbed). They showed a clear impairment of passive avoidance performance model indicating impaired memory processes. The $GABA_BR1$ KO also displayed increased hyperlocomotion and hyperactivity in new environment. Gassmann et al., J Neurosci. 24, 6086-6097, 2004 has shown that $GABA_BR2KO$ mice suffer from spontaneous seizures, hyperalgesia, hyperlocomotor activity and severe memory impairment, comparable to $GABA_BR1KO$ mice. Moreover, altered anxiety and depression behavior was observed in $GABA_BR2KO$ mice (Mombereau et al., Neuroreport, 16, 307-310, 2005) Therefore, heteromeric $GABA_B$ R1R2 receptors are responsible for these phenotypes. The $GABA_BR1$ gene is mapped to chromosome 6p21.3, which is within the HLA class I, a region with linkage for schizophrenia, epilepsy and dyslexia (Peters et al., Neurogenetics, 2, 47-54, 1998). Five single nucleotide polymorphisms (SNPs); the A-7265G (promoter region), C10497G (intron 9), Ser-491-Ser (T to C, exon 12), Phe-659-Phe (A to G, exon 16) and A33795G (3'-UTR) have been found in the $GABA_BR1$ gene. The association of A-7265G polymorphism of $GABA_BR1$ gene with schizophrenia (Zai et al., Eur Neuropsychopharmacol 15, 347-52, 2005) and Obsessive-compulsive disorder (OCD) (Zai et al., Am J Med Genet B Neuropsychiatr Genet 134, 25-29. 2005) have been recently reported.

Baclofen (Lioresal®, β-chlorophenyl GABA), a selective $GABA_B$ receptor agonist with $EC_{50}=210$ nM at native receptor, is the only ligand, which has been used since 1972 in clinical study for the treatment of spasticity and skeletal muscle rigidity in patients following spinal cord injury, multiple sclerosis, amyotrophic lateral sclerosis, cerebral palsy. Most of the preclinical and clinical studies conducted with baclofen and $GABA_B$ receptor agonists were for the treatment of neuropathic pain and alleviating the craving associated with cocaine and nicotine (Misgeld et al., Prog. Neurobiol. 46, 423-462, 1995; Enna et al., Life Sci, 62, 1525-1530, 1998; McCarson and Enna, Neuropharmacology, 38, 1767-1773, 1999; Brebner et al., Neuropharmacology, 38, 1797-1804, 1999; Paterson et al., Psychopharmacology, 172, 179-186, 2004; Paterson et al., Neuropsychopharmacology, 30, 119-128, 2005). In panic disorder patients, Baclofen was shown to be significantly effective in reducing the number of panic attacks and symptoms of anxiety as assessed with the Hamilton anxiety scale, Zung anxiety scale and Katz-R nervousness subscale (Breslow et al., Am. J. Psychiatry, 146, 353-356, 1989). In a study with a small group of veterans with chronic, combat-related posttraumatic stress disorder (PTSD), baclofen was found to be an effective and well-tolerated treatment. It resulted in significant improvements in the overall symptoms of PTSD, most notably the avoidance, emotional numbing and hyperarousal symptoms and also in reduced accompanying anxiety and depression (Drake et al., Ann. Pharmacother. 37, 1177-1181, 2003). In preclinical study, baclofen was able to reverse the reduction in prepulse inhibition (PPI) of the acoustic startle response induced by dizocilpine, but not by apomorphine in rat PPI model of psychosis (Bortolato et al., Psychopharmacology, 171, 322-330, 2004). Therefore, $GABA_B$ receptor agonist has a potential in the pharmacological therapy of psychotic disorders. Because of presence of $GABA_B$ receptors in PNS, preclinical and clinical studies with baclofen have demonstrated therapeutic potential of $GABA_B$ receptor agonist for bladder dysfunction, intestinal and pulmonary disorders such as overactive bladder (bladder function is under tonic $GABA_B$ control), gastroesophageal reflux disease and heartburn, cough and asthma (Bolser et al., *Br J Pharmacol*, 113, 1344-1348, 1994; Dicpinigaitis et al., *J Clin Pharmacol*, 38, 364-367, 1998; Dicpinigaitis et al., *Arch Phys Med Rehabil*, 81, 921-923, 2000; Cange et al., *Aliment Pharmacol Ther*, 16, 869-873, 2002; Lehmann et al., *Eur J Pharmacol*, 448, 67-70, 2002; Pehrson et al., *J Urol*, 168, 2700-2705, 2002; Sanger et al., *Auton Autacoid Pharmacol*, 22, 147-154, 2002; Symonds et al., *Eur J Pharmacol*, 470, 95-97, 2003; Piqueras et al., *Br J Pharmacol*, 142, 1038-48, 2004). Unfortunately, Baclofen has a number of side-effects including poor blood-brain-barrier penetration, very short duration of action and narrow therapeutic window (muscle relaxation, sedation and tolerance) that limit its utility.

Urwyler et al., *Mol. Pharmacol.*, 60, 963-971, 2001 have reported on a novel class of $GABA_B$ receptor ligands, called positive allosteric modulators, CGP7930 [2,6-di-tert-butyl-4-(3-hydroxy-2,2-dimethyl-propyl)-phenol] and its aldehyde analogue CGP13501. These ligands have no effect on their own at $GABA_B$ receptors, but in concert with endogenous GABA, they increase both the potency and maximal efficacy of GABA at the $GABA_B$R1R2 (Pin et al., *Mol. Pharmacol.*, 60, 881-884, 2001). Interestingly, this enhancement of the GABA effect by CGP7930 was further corroborated in an in vivo mechanism-based paradigm, in which pretreatment with CGP7930 resulted in a potentiation of the baclofen-induced loss of righting reflex in DBA mice; this combined effect can be blocked by $GABA_B$ antagonist (Carai et al., *Eur J Pharmacol*, 504, 213-216, 2004). A recent study with CGP7930 (Binet et al., *J Biol Chem.*, 279, 29085-29091, 2004) has shown that this positive modulator activates directly the seven transmembrane domains (7TMD) of $GABA_B$R2 subunit. Mombereau et al., *Neuropsychopharmacology*, 1-13, 2004 have recently reported on the anxiolytic effects of acute and chronic treatment with the $GABA_B$ receptor positive modulator, GS39783 (N,N_-dicyclopentyl-2-methylsulfanyl-5-nitro-pyrimidine-4,6-diamine) (Urwyler et al., *J. Pharmacol. Exp. Ther.*, 307, 322-330, 2003) in the light-dark box and elevated zero maze test models of anxiety. No tolerance after chronic treatment (21 days) with GS39783 (10 mg/kg, P.O., once daily) was observed. Because the $GABA_B$ enhancers have no effect on receptor activity in the absence of GABA, but do enhance allosterically the affinity of the $GABA_B$ receptor for the endogenous GABA, it is expected that these ligands should have an improved side effect profile as compared to baclofen. Indeed, GS39783 at 0.1-200 mg/kg, PO had no effect on spontaneous locomotor activity, rotarod, body temperature and traction test in comparison to baclofen, which showed these side effects at 2.5-15 mg/kg, PO. GS39783 did not have any effect on cognition performance as assessed by passive avoidance behavioral test in mice and rats. Furthermore, GS39783 exhibited anxiolytic-like effects in the elevated plus maze (rat), elevated zero maze (mice and rats), and the stress-induced hyperthermia (mice) test paradigms. Therefore, GS39783 represents a novel anxiolytic without side-effects associated with baclofen or benzodiazepines (Cryan et al., *J Pharmacol Exp Ther.*, 310, 952-963, 2004). The preclinical investigation with the CGP7930 and GS39783 has shown that both compounds were effective at decreasing cocaine self-administration in rats (Smith et al., *Psychopharmacology*, 173, 105-111, 2004). The positive modulator, CGP7930 has also been preclinically studied for the treatment of Gastro-Esophageal Reflux Disease (GERD) and was found to be effective (WO 03/090731, use of $GABA_B$ receptor positive modulators in gastro-intestinal disorders).

Positive allosteric modulators have been reported for other family 3 GPCRs including mGlu1 receptor (Knoflach et al., *Proc. Natl. Acad. Sci., USA*, 98, 13402-13407, 2001; Wichmann et al., *Farmaco*, 57, 989-992, 2002), calcium-sensing receptor (NPS R-467 and NPS R-568) (Hammerland et al., *Mol. Pharmacol.*, 53, 1083-1088, 1998) (U.S. Pat. No. 6,313, 146), mGlu2 receptor [LY487379, N-(4-(2-methoxyphenoxy)-phenyl-N-(2,2,2-trifluoroethylsulfonyl)-pyrid-3-ylmethylamine and its analogs] (WO 01/56990, Potentiators of glutamate receptors) and mGlu5 receptor (CPPHA, N-{4-chloro-2-[(1,3-dioxo-1,3-dihydro-2H-isoindol-2-yl)methyl]phenyl}-2-hydroxybenzamide) (O'Brien et al., *J. Pharmaco. Exp. Ther.*, 27, Jan. 27, 2004). Interestingly, it has been demonstrated that these positive modulators bind to a novel allosteric site located within the 7TMD region, thereby enhancing the agonist affinity by stabilizing the active state of the 7TMD region (Knoflach et al., *Proc. Natl. Acad. Sci., USA* 98, 13402-13407, 2001; Schaffhauser et al., *Mol. Pharmacol.*, 64, 798-810, 2003). Moreover, the NPS R-467, NPS R-568 (Tecalcet) and related compounds represent the first positive allosteric modulators that have entered the clinical trails due to their allosteric mode of action. Sensipar™ (a potentiator of $Ca^{2+}$-sensing receptor, cinacalcet by Amgen-NPS) is the $1^{st}$ positive allosteric modulator of a GPCR approved by the FDA in 2004.

Dyachenko, V. I et al. in Steric effects of ortho substituents in reactions of phenols and phenolates with polyfluoro ketones, Izvestiya Akademii Nauk SSSR, Seriya Khimicheskaya (1989), (4), 923-8 already disclosed (RS)-5,7-Di-tert-butyl-3-hydroxy-3-trifluoromethyl-3H-benzofuran-2-one. Nevertheless Dyachenko, V. I et al. belongs to pure chemistry literature and neither teach nor suggests that said compound may have an activity at the $GABA_B$ receptor.

SUMMARY OF THE INVENTION

The present invention provides compounds of formula I:

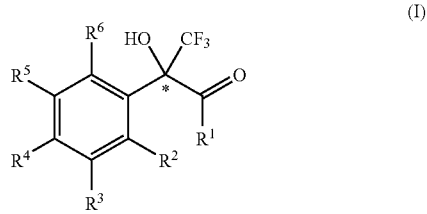

wherein
$R^1$ is H, hydroxy, $C_{1-6}$-alkoxy or $NR^aR^b$, wherein $R^a$ and $R^b$ are each independently H or $C_{1-6}$-alkyl;
$R^2$ is H, hydroxy or F;
or $R^1$ and $R^2$ are together —O— or —NH— thereby forming a 5-membered heterocyclic ring with the carbon atoms to which they are attached;
$R^3$ is t-butyl, 1,1-dimethylpropyl or aryl;
$R^4$ is H;
$R^5$ is $C_{1-6}$-alkyl or $C_{1-6}$-haloalkyl; and
$R^6$ is H, hydroxy or $C_{1-6}$-alkyl;
as well as optical isomers and pharmaceutically acceptable salts thereof, except for (RS)-5,7-Di-tert-butyl-3-hydroxy-3-trifluoromethyl-3H-benzofuran-2-one.

The invention also provides pharmaceutical compositions containing compounds of the invention. The invention further provides processes for the preparation of compounds of the invention and for the manufacture of pharmaceutical compositions containing them.

The compounds of formula I and their salts are distinguished by valuable therapeutic properties. They are active on the $GABA_B$ receptor.

The present invention further provides methods for treating illnesses, such as anxiety, depression, epilepsy, schizophrenia, cognitive disorders, spasticity and skeletal muscle rigidity, spinal cord injury, multiple sclerosis, amyotrophic lateral sclerosis, cerebral palsy, neuropathic pain and craving associated with cocaine and nicotine, psychosis, panic disorder, posttraumatic stress disorders, for bladder dysfunction, intestinal and pulmonary disorders such as overactive bladder, gastroesophageal reflux disease and heartburn, cough and asthma which comprise administering to an individual a therapeutically effective amount of a compound of formula I or of (RS)-5,7-Di-tert-butyl-3-hydroxy-3-trifluoromethyl-3H-benzofuran-2-one or acceptable acid addition salts thereof.

DETAILED DESCRIPTION OF THE INVENTION

The following definitions of the general terms used in the present description apply irrespective of whether the terms in question appear alone or in combination. It must be noted that, as used in the specification and the appended claims, the singular forms "a", "an," and "the" include plural forms unless the context clearly dictates otherwise.

As used herein, the term "aryl" means a monovalent cyclic aromatic hydrocarbon moiety, for example, optionally substituted phenyl or naphthyl. Substituents for aryl include but are not limited to halo, hydroxy, $C_{1-7}$-alkyl, $C_{1-7}$-alkoxy, $C_{1-7}$-haloalkyl, $C_{1-7}$-haloalkoxy as well as those groups specifically illustrated by the examples herein below with the examples.

"$C_{1-6}$-alkyl" denotes a straight- or branched-carbon chain hydrocarbon group containing from 1 to 6 carbon atoms, preferably 1 to 4 carbon atoms. Examples of such groups are are methyl, ethyl, propyl, isopropyl, isobutyl, sec-butyl, tert-butyl, pentyl, and n-hexyl as well as those specifically illustrated by the examples herein below.

"Halogen" or "halo" denotes chlorine, fluorine, bromine, or iodine.

"$C_{1-6}$-haloalkyl" denotes a $C_{1-6}$-alkyl group as defined above which is substituted by one or more halogen atom. Examples of $C_{1-6}$-haloalkyl include, but are not limited to, methyl, ethyl, propyl, isopropyl, isobutyl, sec-butyl, tert-butyl, pentyl or n-hexyl substituted by one or more Cl, F, Br or I atom(s) as well as those groups specifically illustrated by the examples herein below. Preferred $C_{1-6}$-haloalkyl are difluoro- or trifluoro-methyl or ethyl.

"$C_{1-6}$-alkoxy" denotes a group wherein the alkyl group is as defined above, which is connected via an oxygen atom. Preferred $C_{1-6}$-alkoxy are MeO— and Et-O as well as those groups specifically illustrated by the examples herein below.

"Hydroxy" denotes one, two or three —OH group(s).

The expression "$R^1$ and $R^2$ are together —O— or —NH— thereby forming a 5-membered heterocyclic ring with the carbon atoms to which they are attached" means one of the groups of the following formula:

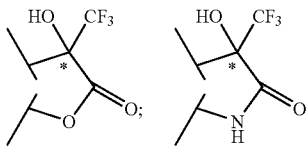

"Pharmaceutically acceptable" such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, which include but are not limited to hydrochloric acid, nitric acid, sulfuric acid, phosphoric acid, citric acid, formic acid, fumaric acid, maleic acid, acetic acid, succinic acid, tartaric acid, methane-sulfonic acid, p-toluenesulfonic acid.

"Therapeutically effective amount" means an amount that is effective to prevent, alleviate or ameliorate symptoms of disease or prolong the survival of the subject being treated.

The present invention provides compounds of formula I:

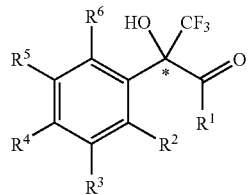

(I)

wherein
$R^1$ is H, hydroxy, $C_{1-6}$-alkoxy or $NR^aR^b$, wherein $R^a$ and $R^b$ are each independently H or $C_{1-6}$-alkyl;
$R^2$ is H, hydroxy or F;
or $R^1$ and $R^2$ are together —O— or —NH— thereby forming a 5-membered heterocyclic ring with the carbon atoms to which they are attached;
$R^3$ is t-butyl, 1,1-dimethylpropyl or aryl;
$R^4$ is H;
$R^5$ is $C_{1-6}$-alkyl or $C_{1-6}$-haloalkyl; and
$R^6$ is H, hydroxy or $C_{1-6}$-alkyl;
as well as optical isomers and pharmaceutically acceptable salts thereof, except for (RS)-5,7-Di-tert-butyl-3-hydroxy-3-trifluoromethyl-3H-benzofuran-2-one.

In certain embodiments, the compounds according to the invention are those compounds of formula I wherein:
$R^1$ is H, hydroxy, $C_{1-6}$-alkoxy or $NR^aR^b$, wherein $R^a$ and $R^b$ are independently H or $C_{1-6}$-alkyl;
$R^2$ is H, hydroxy or F;
$R^3$ is t-butyl, 1,1-dimethylpropyl or aryl;
$R^4$ is H;
$R^5$ is $C_{1-6}$-alkyl or $C_{1-6}$-haloalkyl; and
$R^6$ is H, hydroxy or $C_{1-6}$-alkyl;
as well as optical isomers and pharmaceutically acceptable salts thereof, for example the following compounds:
(R,S)-2-(3,5-Di-tert-butyl-2-hydroxy-phenyl)-3,3,3-trifluoro-2-hydroxy-propionic acid;
(R,S)-2-(3,5-Di-tert-butyl-2-hydroxy-phenyl)-3,3,3-trifluoro-2-hydroxy-propionic acid, sodium salt;
(R,S)-2-(3,5-Di-tert-butyl-phenyl)-3,3,3-trifluoro-2-hydroxy-propionic acid methyl ester; and
(R,S)-2-(3,5-Di-tert-butyl-phenyl)-3,3,3-trifluoro-2-hydroxy-propionic acid.

Also encompassed by the compounds of formula I are the compounds of formula I-a according to the invention:

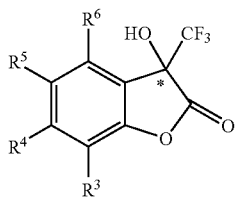

(I-a)

wherein,
R³ is t-butyl, 1,1-dimethylpropyl or aryl;
R⁴ is H;
R⁵ is $C_{1-6}$-alkyl or $C_{1-6}$-haloalkyl; and
R⁶ is H, hydroxy or $C_{1-6}$-alkyl;
as well as optical isomers and pharmaceutically acceptable salts thereof, except for (RS)-5,7-Di-tert-butyl-3-hydroxy-3-trifluoromethyl-3H-benzofuran-2-one, for example the following compounds:
(R,S)-5-tert-Butyl-3-hydroxy-7-phenyl-3-trifluoromethyl-3H-benzofuran-2-one;
(R,S)-5,7-Di-tert-butyl-3-hydroxy-3-trifluoromethyl-3H-benzofuran-2-one;
(S)-(−)-5,7-Di-tert-butyl-3-hydroxy-3-trifluoromethyl-3H-benzofuran-2-one;
(R,S)-7-tert-Butyl-3-hydroxy-5-methyl-3-trifluoromethyl-3H-benzofuran-2-one;
(R,S)-5,7-Bis-(1,1-dimethyl-propyl)-3-hydroxy-3-trifluoromethyl-3H-benzofuran-2-one;
(R)-(+)-5,7-Di-tert-butyl-3-hydroxy-3-trifluoromethyl-3H-benzofuran-2-one;
(R,S)-5,7-Di-tert-butyl-3,4-dihydroxy-3-trifluoromethyl-3H-benzofuran-2-one; and
(R,S)-7-tert-Butyl-5-ethyl-3-hydroxy-3-trifluoromethyl-3H-benzofuran-2-one.

Also encompassed by the compounds of formula I are the compounds of formula I-b according to the invention:

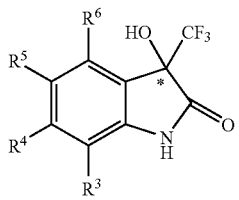

(I-b)

wherein,
R³ is t-butyl, 1,1-dimethylpropyl or aryl;
R⁴ is H;
R⁵ is $C_{1-6}$-alkyl or $C_{1-6}$-haloalkyl; and
R⁶ is H, hydroxy or $C_{1-6}$-alkyl;
as well as optical isomers and pharmaceutically acceptable salts thereof, for example (R,S)-5,7-di-tert-butyl-3-hydroxy-3-trifluoromethyl-1,3-dihydro-indol-2-one.

The invention also encompasses processes for the preparation of the compounds of the invention as follows:

In a certain embodiment, the process of the invention for preparing compounds of formula I comprises reacting a compound of formula II

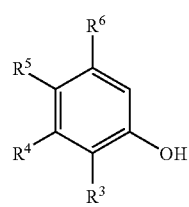

II with a compound of formula $CF_3COCOR^1$, to obtain a compound of formula I, wherein R¹ is $C_{1-6}$-alkoxy, R² is OH and R³ to R⁶ are as defined hereinabove.

In a certain embodiment, the process of the invention for preparing compounds of formula I comprises reacting a compound of formula III

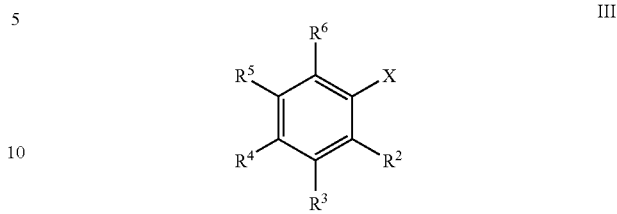

III wherein X is Br or I, with a compound of formula $CF_3COCOR^1$ to obtain a compound of formula I, wherein R¹ is $C_{1-6}$-alkoxy and R² to R⁶ are as defined hereinabove.

In a certain embodiment, the process of the invention for preparing compounds of formula I-a comprises the cyclization reaction of a compound of formula I:

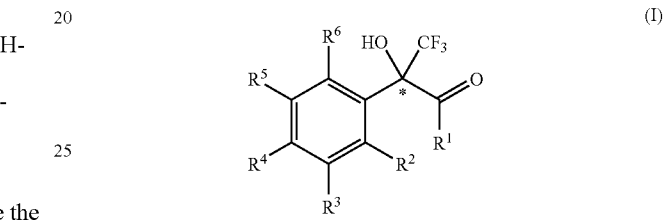

(I)

wherein R¹ is $C_{1-6}$-alkoxy and R² is OH, into a compound of formula I-a, wherein R² to R⁶ are as defined hereinabove.

In a certain embodiment, the process of the invention for preparing compounds of formula I comprises hydrolyzing the R¹ moiety which is a $C_{1-6}$-alkoxy in a compound of formula I:

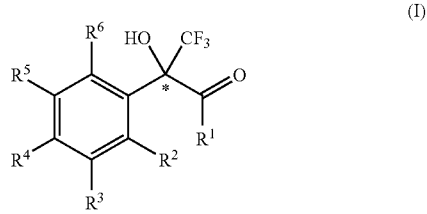

(I)

to obtain a compound of formula I, wherein R¹ is hydroxy and R² to R⁶ are as defined hereinabove.

The invention also encompasses a compound of formula I, I-a or I-b, whenever it is prepared according to the above-mentioned process.

The following general schemes 1 to 3 further illustrate certain embodiments of the preparation of the compounds according to the invention. In these schemes, and unless otherwise stated, all starting materials, building blocks and intermediates are commercially available. Further, still in these schemes and unless otherwise stated R¹ to R⁶ are as defined hereinabove.

Scheme 1

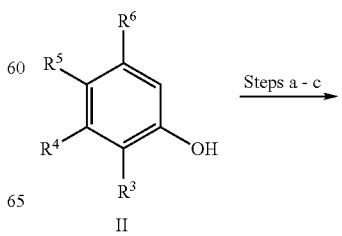

II

-continued

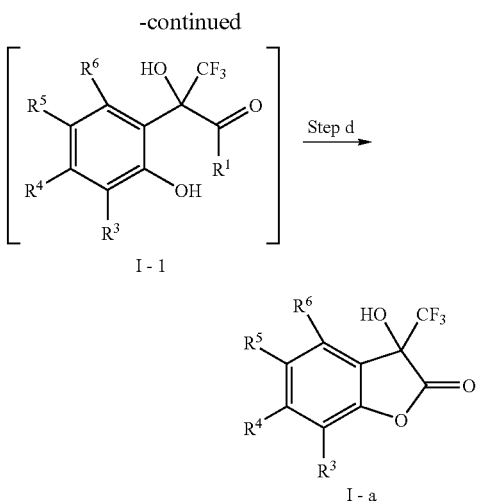

a. BuLi (1 eq), THF, −70° to 20° or TMSONa (1 eq), DCE
b. GaCl₃ (1 eq), DCE, −10° to 80°, 15 min.
c. CF₃COCOR¹ (R¹ = C$_{1-6}$-alkoxy) (1 eq), DCE, 0° − 20°, 2-4 h
d. DCE, 80°, 2-16 h Steps a-d:

Optimizing a procedure by G. Casiraghi, G. Sartori, G. Casnati, F. Bigi, *JCS Perkin Transactions* 1(1972-1999) 1983, 1649-1651. First the lithium salt of the starting phenol was prepared in tetrahydrofuran (THF) with n-butyllithium, then the solvent tetrahydrofuran was exchanged with 1,2-dichloroethane. The reaction did not work in toluene. Alternatively, the sodium salt of the starting phenol was prepared with sodium trimethylsilanolate directly in 1,2-dichloroethane, but the reaction was not generally applicable and gave different regioisomeric products. Then the Lewis acid, gallium(III) chloride or aluminium(III) chloride was added. Subsequent short heating formed the complex of the Lewis acid with the phenolate and LiCl was precipitated. This complex was reacted with methyl trifluoropyruvate at 0° C. to ambient temperature, and the intermediate was cyclized in situ by heating at reflux for 2 to 16 h.

Scheme 2

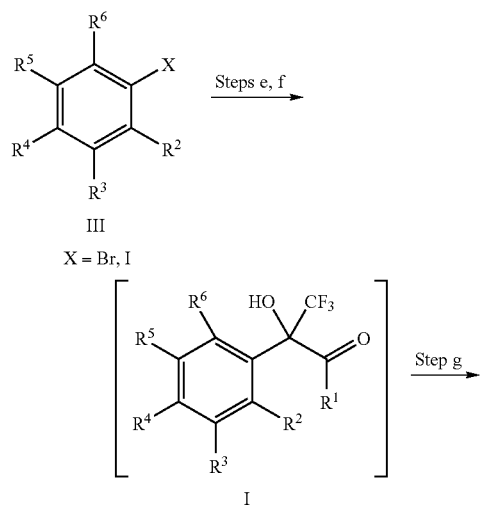

-continued

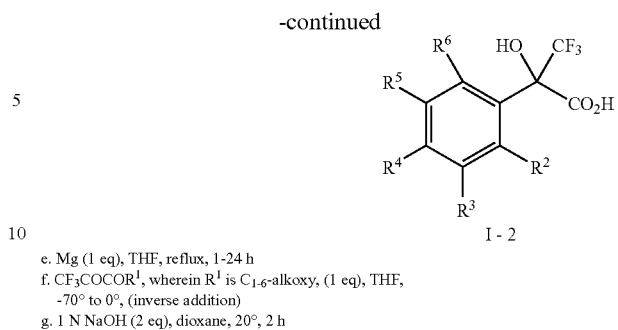

e. Mg (1 eq), THF, reflux, 1-24 h
f. CF₃COCOR¹, wherein R¹ is C$_{1-6}$-alkoxy, (1 eq), THF, −70° to 0°, (inverse addition)
g. 1 N NaOH (2 eq), dioxane, 20°, 2 h Steps e and f:

In the first flask a classical aryl Grignard reagent was prepared in THF with magnesium turnings from a bromo- or iodoarene. This Grignard solution was added slowly to a −70° C. cold solution of methyl- or ethyl trifluoropyruvate in THF (inverse addition).

Step g:

The ester was readily hydrolyzed with aqueous 1 N NaOH in dioxane at ambient temperature.

Scheme 3

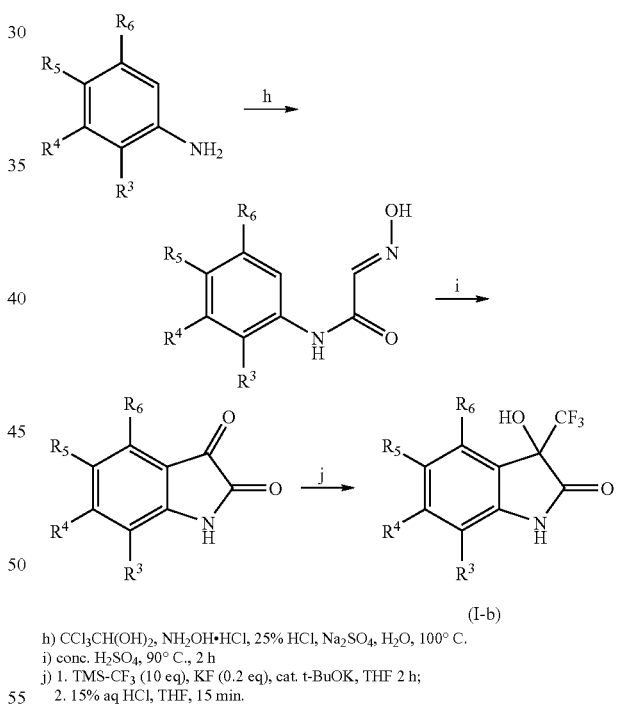

h) CCl₃CH(OH)₂, NH₂OH·HCl, 25% HCl, Na₂SO₄, H₂O, 100° C.
i) conc. H₂SO₄, 90° C., 2 h
j) 1. TMS-CF₃ (10 eq), KF (0.2 eq), cat. t-BuOK, THF 2 h;
   2. 15% aq HCl, THF, 15 min.

Steps h and i:

This two step process, known in the art as Sandmeyer isatin synthesis was most recently applied by K. C. Nicolaou, D. Y. K. Chen, X. Huang, T. Ling, M. Bella, S. A. Snyder, J. Am. Chem. Soc. 2004, 126, 12888-12896. Alternative routes are proposed in the reference by Nicolaou. The low yield obtained in the example A.1 can be rationalized by the low solubility of the highly lipophilic starting material 2,4-di-tert-butyl-phenylamine in the aqueous reaction medium.

Step j:

Following a procedure by I. Choudhury-Mukherjee, H. A. Schenck, S. Cechova, T. N. Pajewski, J. Kapur, J. Ellena, D. S. Cafiso, M. L. Brown, *J Med. Chem.* 2003, 46, 2494-2501.

As mentioned earlier, the compounds of formula I, I-a and I-b and their pharmaceutically acceptable addition salts possess valuable pharmacological properties. It has been found that the compounds of the present invention have an affinity to the $GABA_B$ receptor.

The compounds were investigated in accordance with the tests given hereinafter.

Intracellular $Ca^{2+}$ Mobilization Assay

The Chinese Hamster Ovary (CHO) cells stably expressing human $GABA_BR1aR2a$ and $G\alpha16$ were seeded at $5\times10^4$ cells/well in the poly-D-lysine treated, 96-well, black/clear-bottomed plates (BD Biosciences, Palo Alto, Calif.). 24 h later, the cells were loaded for 90 min at 37° C. with 4 µM Flou-4 acetoxymethyl ester (Catalog No. F-14202, Molecular Probes, Eugene, Oreg.) in loading buffer (1×HBSS, 20 mM HEPES, 2.5 mM Probenecid). Hanks' Balanced Salt Solution (HBSS) (10×) (catalog No. 14065-049) and HEPES (1M) (catalog No. 15630-056) were purchased from Invitrogen, Carlsbad, Calif. Probenecid (250 mM) (catalog No. P8761) was from Sigma, Buchs, Switzerland. The cells were washed five times with loading buffer to remove excess dye and intracellular calcium mobilization, $[Ca^{2+}]_i$ were measured using a Fluorometric Imaging Plate Reader (FLIPR, Molecular Devices, Menlo Park, Calif.) as described previously (Porter et al., Br. J. Pharmacol., 128, 13-20, 1999). The enhancers were applied 15 min before the application of the GABA. For GABA shift assay, concentration-response curves of GABA (0.0003-30 µM) were determined in the absence and presence of 10 µM enhancer. The GABA-shift is defined as Log [$EC_{50}$ (GABA+10 µM enhancer)/$EC_{50}$ (GABA alone)]. The % maximum enhancing effect (% $E_{max}$) and potency ($EC_{50}$ value) of each enhancer was determined from concentration-response curve of the enhancer (0.001-30 µM) in the presence of 10 nM GABA ($EC_{10}$). Responses were measured as peak increase in fluorescence minus basal, normalized to the maximal stimulatory effect induced by 10 µM GABA alone (considered 100%) and 10 nM GABA alone (considered 0%). The data were fitted with the equation $Y=100+(Max-100)/(1+(EC_{50}/[drug])^n)$ where Max is the maximum effect, $EC_{50}$ the concentration eliciting a half-maximum effect and n the Hill slope.

| | Intracellular $Ca^{2+}$ mobilization Assay in $CHO-GABA_BR1aR2a-G\alpha16$ cell | | GABA shift |
|---|---|---|---|
| Example | $E_{max}$ (%) at 10 nM GABA alone = 0% 10 µM GABA alone = 100% | $EC_{50}$ (µM) at 10 nM GABA | Log [$EC_{50}$ (GABA + 10 µM cp)/ $EC_{50}$ (GABA alone)] |
| 1 | 52 | 0.15 | −1 |
| 3 | 70 | 0.32 | −1 |
| 6 | 41 | 4.5 | −0.5 |
| 7 | 66 | 2.1 | −0.9 |
| 9 | 62 | 0.36 | −1.3 |

The present invention also provides pharmaceutical compositions containing compounds of formula I, I-a and Ib or a pharmaceutically acceptable salts thereof and a pharmaceutically acceptable carrier. Such pharmaceutical compositions can be in the form of tablets, coated tablets, dragées, hard and soft gelatin capsules, solutions, emulsions or suspensions. The pharmaceutical compositions also can be in the form of suppositories or injectable solutions.

The pharmaceutical compositions of the invention, in addition to one or more compounds of the invention, contain a pharmaceutically acceptable carrier. Suitable pharmaceutically acceptable carriers include pharmaceutically inert, inorganic or organic excipients for the production of tablets, coated tablets, dragees and hard gelatin capsules. Lactose, corn starch or derivatives thereof, talc, stearic acid or its salts etc can be used as such excipients e.g. for tablets, dragees and hard gelatin capsules. Suitable excipients for soft gelatin capsules are e.g. vegetable oils, waxes, fats, semi-solid and liquid polyols. Suitable excipients for the manufacture of solutions and syrups include but are not limited to water, polyols, saccharose, invert sugar, glucose. Suitable excipients for injection solutions include but are not limited to water, alcohols, polyols, glycerol, vegetable oils. Suitable excipients for suppositories include but are not limited to natural or hardened oils, waxes, fats, semi-liquid or liquid polyols.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a method for the manufacture of pharmaceutical compositions. Such process comprises bringing one or more compounds of formula I and/or pharmaceutically acceptable acid addition salts thereof and, if desired, one or more other therapeutically valuable substances into a galenical administration form together with one or more therapeutically inert carriers.

The compounds and compositions of the present invention can be administered in a conventional manner, for example, orally, rectally, or parenterally. The pharmaceutical compositions of the invention can be administered orally, for example, in the form of tablets, coated tablets, dragees, hard and soft gelatin capsules, solutions, emulsions, or suspensions. The pharmaceutical compositions also can be administered rectally, for example, in the form of suppositories, or parenterally, for example, in the form of injectable solutions.

The compounds of formula I and their salts are active on the $GABA_B$ receptor. The present invention provides methods for treating illnesses, such as anxiety, depression, epilepsy, schizophrenia, cognitive disorders, spasticity and skeletal muscle rigidity, spinal cord injury, multiple sclerosis, amyotrophic lateral sclerosis, cerebral palsy, neuropathic pain and craving associated with cocaine and nicotine, psychosis, panic disorder, posttraumatic stress disorders, for bladder dysfunction, intestinal and pulmonary disorders such as overactive bladder, gastroesophageal reflux disease and heartburn, cough and asthma which comprise administering to an individual a therapeutically effective amount of a compound of formula I or of (RS)-5,7-Di-tert-butyl-3-hydroxy-3-trifluoromethyl-3H-benzofuran-2-one or acceptable acid addition salts thereof.

The dosage at which a compound of the invention is administered can vary within wide limits and will, of course, be fitted to the individual requirements in each particular case. In general, in the case of oral administration a daily dosage of about 10 to 1000 mg per person of a compound of general formula I should be appropriate, although the above upper limit can also be exceeded when necessary.

Tablet Formulation (Wet Granulation)

| | | mg/tablet | | |
|---|---|---|---|---|
| Item | Ingredients | 5 mg | 25 mg | 100 mg | 500 mg |
| 1. | Compound of formula I | 5 | 25 | 100 | 500 |
| 2. | Lactose Anhydrous DTG | 125 | 105 | 30 | 150 |
| 3. | Sta-Rx 1500 | 6 | 6 | 6 | 30 |
| 4. | Microcrystalline Cellulose | 30 | 30 | 30 | 150 |
| 5. | Magnesium Stearate | 1 | 1 | 1 | 1 |
| | Total | 167 | 167 | 167 | 831 |

Manufacturing Procedure
1. Mix items 1, 2, 3 and 4 and granulate with purified water.
2. Dry the granules at 50° C.
3. Pass the granules through suitable milling equipment.
4. Add item 5 and mix for three minutes; compress on a suitable press.

Capsule Formulation

| | | mg/capsule | | |
|---|---|---|---|---|
| Item | Ingredients | 5 mg | 25 mg | 100 mg | 500 mg |
| 1. | Compound of formula I | 5 | 25 | 100 | 500 |
| 2. | Hydrous Lactose | 159 | 123 | 148 | — |
| 3. | Corn Starch | 25 | 35 | 40 | 70 |
| 4. | Talc | 10 | 15 | 10 | 25 |
| 5. | Magnesium Stearate | 1 | 2 | 2 | 5 |
| | Total | 200 | 200 | 300 | 600 |

Manufacturing Procedure
1. Mix items 1, 2 and 3 in a suitable mixer for 30 minutes.
2. Add items 4 and 5 and mix for 3 minutes.
3. Fill into a suitable capsule.

EXAMPLES

Synthesis of Intermediates

Example A.1

N-(2,4-Di-tert-butyl-phenyl)-2-[(E)-hydroxyimino]-acetamide

Sodium sulfate (20.75 g, 146 mmol) and chloral hydrate (2.78 g, 17 mmol) were dissolved in water (30 mL). Then a solution of 2,4-di-tert-butyl-phenylamine [prepared according to P. D. Bartlett, M. Roha, R. M. Stiles, *J. Am. Chem. Soc.* 1954, 76, 2349-2353] (3 g, 14.6 mmol) in water (6 mL), 25% HCl (1.9 mL), and a solution of hydroxylamine hydrochloride (3.25 g, 47 mmol) in water (8 mL) were added. The mixture was heated at 100° C. for 1 h. Extraction with ethyl acetate and chromathography on silica gel with a gradient of 0% to 25% of ethyl acetate in heptane afforded a light brown solid (1 g, 25%), which was a 1:1-mixture with formylated starting material. MS: m/z=277 (M+H).

Example A.2

5,7-Di-tert-butyl-1H-indole-2,3-dione

N-(2,4-Di-tert-butyl-phenyl)-2-[(E)-hydroxyimino]-acetamide (500 mg, 1.7 mmol) in concentrated sulfuric acid (3.8 mL) was heated at 90° C. for 2 h. This solution was cooled at 0° C. and slowly added to ice-water (15 mL), the brown precipitate was filtered off and purified by chromathography on silica gel with a gradient of 0% to 25% of ethyl acetate in heptane to afford 200 mg (42%) of an orange powder. MS: m/z=259 (M).

Synthesis of the Compounds of Formula I According to the Invention

In the following examples, unless otherwise specified, all the starting materials are commercially available.

Example 1

(R,S)-5,7-Di-tert-butyl-3-hydroxy-3-trifluoromethyl-3H-benzofuran-2-one 2,4-Di-tert-butylphenol (28 g, 28.5 mmol) was dissolved in tetrahydrofuran (250 mL) under argon and cooled to −70°. A 1.6 M solution of butyllithium in hexane (85 mL, 135.7 mmol) was added and the solution was allowed to reach 20° C. Tetrahydrofuran was distilled off and replaced by 1,2-dichloroethane (250 mL), which was distilled off again and replaced with 1,2-dichloroethane (250 mL). After cooling in ice/MeOH a fresh ampoule of gallium(III)chloride (25 g, 142.5 mmol) was added (exothermic, 5° C.). The resulting solution was refluxed for 15 min. affording a white precipitate of LiCl. The suspension was cooled in ice, then methyl trifluoropyruvate (14.5 mL, 142.5 mmol) dissolved in 1,2-dichloroethane (20 mL) was added and stirring continued for 13 h at 20° C. The reaction was driven to completion by refluxing for 3.5 h. After cooling, the suspension was extracted with dichloromethane (2×), cold 1 M HCl (2×), NaCl (1×). The crude product was purified by chromatography on silica gel in heptane/dichloromethane 2:1. The purified product (37 g) was recrystallized from cold heptane (150 mL), and dried at 50° C./1 mbar for 5 h. One obtained 28.9 g (64%) of white crystals, m.p. 83° C. MS: m/z=330 (M).

Example 2

(R,S)-5-tert-Butyl-3-hydroxy-7-phenyl-3-trifluoromethyl-3H-benzofuran-2-one 4-tert-Butyl-2-phenylphenol (4.5 g, 20 mmol) was dissolved in tetrahydrofuran (50 mL) under argon and cooled to −70°. Then 1.6 M solution of butyllithium in hexane (13.8 mL, 22 mmol) was added and the solution was allowed to reach 20° C. Tetrahydrofuran was distilled off and replaced by 1,2-dichloroethane (100 mL, repeated twice). After cooling in ice, aluminum(III)chloride (2.9 g, 22 mmol) was added (not exothermic). The resulting solution was refluxed for 15 min. affording a precipitate of LiCl. The suspension was cooled in ice, then methyl trifluoropyruvate (2.2 mL, 22 mmol) was added and stirring continued for 0.5 h at 20° C. and then refluxed for 3 h. After cooling, the suspension was extracted with dichloromethane (3×), cold 1 M HCl (1×), NaCl (1×). The crude product was purified by chromatography on silica gel in heptane/ethyl acetate 5:1. One obtained 3.14 g (45%) of white crystals. MS: m/z=350 (M).

Example 3

(R,S)-2-(3,5-Di-tert-butyl-2-hydroxy-phenyl)-3,3,3-trifluoro-2-hydroxy-propionic acid (R,S)-5,7-Di-tert-butyl-3-hydroxy-3-trifluoromethyl-3H-benzofuran-2-one (330 mg, 1 mmol) was dissolved in dioxane (2 mL), cooled in ice and treated with 1 N NaOH (2 mL). Stirring without cooling was continued for 6 h. Extraction: ethyl acetate (2×), 1 N HCl (1×), and sat. NaCl (1×). The crude product was purified by chromatography on silica gel with a heptane/ethyl acetate gradient 33:67 to 0:100. One obtained 305 mg (87%) of a light brown foam.

Example 4

(R,S)-2-(3,5-Di-tert-butyl-2-hydroxy-phenyl)-3,3,3-trifluoro-2-hydroxy-propionic acid, Sodium Salt (R,S)-5,7-Di-tert-butyl-3-hydroxy-3-trifluoromethyl-3H-benzofuran-2-one (7.69 g, 23.3 mmol) was dissolved in dioxane (50 mL), cooled in ice and treated with 1 N NaOH (51.2 mL, 51.2 mmol) and stirred for 16 h at 20° C. The yellow solution was evaporated to dryness. The residue was heated to 100° C. in toluene (100 mL) and the hot solution was filtered. The filtrate was evaporated to dryness and the resulting white solid heated to 80° C. in heptane (100 mL). The slurry was allowed to cool to 20° C. and then stirred in ice for 15 min. The white solid was filtered off and washed with little heptane. One obtained 8.87 g (97%) of a white solid. MS: m/z=347 (M−H).

Example 5

(R)-(+)-5,7-Di-tert-butyl-3-hydroxy-3-trifluoromethyl-3H-benzofuran-2-one (R,S)-5,7-Di-tert-butyl-3-hydroxy-3-trifluoromethyl-3H-benzofuran-2-one (1.5 g, 4.5 mmol) was separated on Chiralpack AD with heptane/2-propanol 97:3. The (+)-enantiomer was eluted first (534 mg, 35%), followed by the (−)-isomer (580 mg, 39%), both as white crystals. MS: m/z=330 (M). $[\alpha]_D^{20}$=+33.47 (CHCl$_3$, c=0.765)

Determination of the Absolute Configuration of (R)-(+)-5,7-Di-tert-butyl-3-hydroxy-3-trifluoromethyl-3H-benzofuran-2-one Via X-ray Analysis of (R)-5-(3,5-Di-tert-butyl-2-hydroxy-phenyl)-3-((R)-1-naphthalen-1-yl-ethyl)-5-trifluoromethyl-oxazolidine-2,4-dione (R)-(+)-5,7-Di-tert-butyl-3-hydroxy-3-trifluoromethyl-3H-benzofuran-2-one (100 mg, 0.3 mmol), (R)-(−)-1-(1-naphthyl)ethyl isocyanate (58 uL, 0.33 mmol), and 4-dimethylaminopyridine (3.7 mg, 0.03 mmol) were heated at reflux in toluene (1 mL) for 1 h under nitrogen. The resulting solution was evaporated to dryness and the residue purified by chromatography on silica gel with a gradient of ethyl acetate in heptane from 0% to 100% in 20 min. and then with heptane/DCM 3:1. One obtained 60 mg (37%) of white crystals. Crystals suitable for X-ray analysis were obtained by slow evaporation of a solution in dichloromethane.

Example 6

(S)-(−)-5,7-Di-tert-butyl-3-hydroxy-3-trifluoromethyl-3H-benzofuran-2-one (R,S)-5,7-Di-tert-butyl-3-hydroxy-3-trifluoromethyl-3H-benzofuran-2-one (1.5 g, 4.5 mmol) was separated on Chiralpack AD with heptane/2-propanol 97:3. The (+)-enantiomer was eluted first (534 mg, 35%), followed by the (−)-isomer (580 mg, 39%), both as white crystals. MS: m/z=330 (M). $[\alpha]_D^{20}$=−33.27 (CHCl$_3$, c=0.679)

Example 7

(R,S)-2-(3,5-Di-tert-butyl-phenyl)-3,3,3-trifluoro-2-hydroxy-propionic acid methyl ester Magnesium turnings (536 mg, 22 mmol) were suspended in tetrahydrofuran (20 mL) under nitrogen, a solution of 1-bromo-3,5-di-tert-butylbenzene (5.4 g, 20 mmol) in tetrahydrofuran (20 mL) was added slowly and the reaction started by the addition of a catalytic amount of isopropylmagnesium chloride (0.5 mL, 0.8 mmol) while heating at 50° C. The resulting brown solution was heated at reflux for 30 min to complete the dissolution of the magnesium turnings. The resulting brown Grignard solution was cooled to −70° C. and then transferred via interconnecting teflon tube to the second flask containing methyl trifluoropyruvate (2.25 mL, 22 mmol) dissolved in tetrahydrofuran (20 mL) and cooled under nitrogen to −70° C. Upon mixing the inside temperature reached −30° C., stirring was continued until 0° C. was reached, followed by quenching with sat. NH$_4$Cl solution. Extraction: ethyl acetate (2×), sat. NH$_4$Cl solution (1×), sat. NaCl solution. Chromatography: silica gel, heptane/DCM gradient 100:0 to 0:100 in 40 min. One obtained 3.1 g (45%) of a faint yellow oil. MS: m/z=346 (M).

Example 8

(R,S)-2-(3,5-Di-tert-butyl-phenyl)-3,3,3-trifluoro-2-hydroxy-propionic acid (R,S)-2-(3,5-Di-tert-butyl-phenyl)-3,3,3-trifluoro-2-hydroxy-propionic acid methyl ester (3.1 g, 8.9 mmol) was dissolved in dioxane (20 mL), and treated with 1 N NaOH (20 mL) for 2.5 h at 20° C. The reaction mixture was evaporated to dryness. Extraction: toluene (2×), 1 M KHSO$_4$ (1×), sat. NaCl (1×). The crude product was crystallized from hot heptane. One obtained 2.35 g (79%) of white crystals. MS: m/z=331 (M−H).

Example 9

(R,S)-7-tert-Butyl-3-hydroxy-5-methyl-3-trifluoromethyl-3H-benzofuran-2-one 2-tert-Butyl-4-methylphenol (4.65 g, 28 mmol) was dissolved under nitrogen atmosphere in 1,2-dichloroethane (100 mL) and cooled in ice. Then sodium trimethylsilanolate (3.176 g, 28 mmol) was added (not exothermic), and stirring without cooling was continued for 1 h. The resulting suspension was cooled to −40° C., and a fresh ampoule of granular gallium (III) chloride (5 g, 28.4 mmol) was added (exothermic to −30° C.).The resulting suspension was allowed to warm up to 20° C., and then heated at reflux for 30 min. After cooling in ice, ethyl trifluoropyruvate (4.815 g, 28 mmol) was added and stirring without cooling continued for 2 h and then heated to 80° C. for an hour. After flash chromatography on silica gel with a gradient of 0% to 100% of ethyl acetate in heptane one obtained 2.6 g (32%) of a grey solid. MS: m/z=288 (M).

Example 10

(R,S)-5,7-Di-tert-butyl-3-hydroxy-3-trifluoromethyl-1,3-dihydro-indol-2-one

A flask under a nitrogen atmosphere was charged with anhydrous potassium fluoride (9 mg, 0.15 mmol). A solution of 5,7-di-tert-butyl-1H-indole-2,3-dione (200 mg, 0.77 mmol) in dry tetrahydrofuran (4 mL) was added dropwise via syringe, followed by a solution of (trifluoromethyl)trimethylsilane 2M in tetrahydrofuran (0.58 mL, 1.16 mmol). Upon addition of a saturated solution of potassium tert-butoxide in tetrahydrofuran (0.8 mL), the reaction warmed to 50° C., then the mixture was stirred for 2 h at 20° C., extracted with ethyl acetate (2×20 mL), dried, filtered and concentrated. The crude product was dissolved in dry tetrahydrofuran (2 mL), cooled to 0° C., 3N HCl (0.3 mL) was added and allowed to stir for 15 min. The mixture was extracted with ethyl acetate (2×20 mL). Chromathography on silica gel with heptane/ethyl acetate 100:0 to 80:20 to gave a light yellow solid (120 mg, 47%). MS: m/z=329 (M).

Example 11

(R,S)-5,7-Bis-(1,1-dimethyl-propyl)-3-hydroxy-3-trifluoromethyl-3H-benzofuran-2-one 2,4-Di-tert-pentylphenol (2.37 g, 10 mmol) was dissolved under nitrogen atmosphere in 1,2-dichloroethane (50 mL) and cooled in ice. Then sodium trimethylsilanolate (1.134 g, 10 mmol) was added (not exothermic), and stirring without cooling was continued for 1 h. The resulting suspension was cooled to −40° C., and a fresh ampoule of granular gallium (III) chloride (1.78 g, 10 mmol) was added (exothermic to −30° C.). The resulting suspension was allowed to warm up to 20° C., and then heated at reflux for 30 min. After cooling in ice, ethyl trifluoropyruvate (1.72 g, 10 mmol) was added and stirring without cooling continued for 2 h. The mixture was then heated for one hour at 80° C. One obtained 0.785 g (22%) of a colorless oil. MS: m/z=358 (M).

Example 12

(R,S)-5,7-Di-tert-butyl-3,4-dihydroxy-3-trifluoromethyl-3H-benzofuran-2-one 4,6-Di(tert-butyl)benzene (6.35 g, 28 mmol) was dissolved in tetrahydrofuran (60 mL) under argon and cooled to −70° C. A 1.6 M solution of butyllithium in hexane (37.4 mL, 60 mmol) was added and the solution was allowed to reach 20° C. Tetrahydrofuran was distilled off and replaced by 1,2-dichloroethane (100 mL, repeated twice). After cooling in ice/MeOH, a fresh ampoule of gallium (III) chloride (10 g, 57 mmol) was added (exothermic, 5° C.). The resulting solution was refluxed for 15 min affording a white precipitate of LiCl. The suspension was cooled in ice, then ethyl trifluoropyruvate (4.85 g, 29 mmol) was added and stirring continued for 20 h at 20° C. The reaction was driven to completion by refluxing for 3 h. After cooling, the suspension was extracted with dichloromethane (3×), cold 1M HCl (1×), and saturated NaCl solution (1×). The crude product was purified by flash chromatography on silica gel using a gradient of 0% to 100% of dichloromethane in heptane. One obtained 2.99 g (30%) of a light brown yellow solid. MS: m/z=288 (M).

Example 13

(R,S)-7-tert-Butyl-5-ethyl-3-hydroxy-3-trifluoromethyl-3H-benzofuran-2-one 2-tert-Butyl-4-ethylphenol (3 g, 28 mmol) was dissolved in tetrahydrofuran (60 mL) under argon and cooled to −70° C. A 1.6 M solution of butyllithium in hexane (10.5 mL, 17 mmol) was added and the solution was allowed to reach 20° C. Tetrahydrofuran was distilled off and replaced by 1,2-dichloroethane (100 mL, repeated twice). After cooling in ice/MeOH, a fresh ampoule of gallium (III) chloride(3 g, 17 mmol) was added (exothermic, 5° C.). The resulting solution was refluxed for 15 min affording a white precipitate of LiCl. The suspension was cooled in ice, then ethyl trifluoropyruvate (3.15 g, 19 mmol) was added and stirring continued for 20 h at 20° C. The reaction was driven to completion by refluxing for 3 h. After cooling, the suspension was extracted with dichloromethane (3×), cold 1M HCl (1×), and sat. NaCl solution (1×). The crude product was purified by flash chromatography on silica gel using a gradient of 0% to 100% of dichloromethane in heptane. One obtained 1.54 g (30%) of a colorless gum. MS: m/z=302 (M).

The invention claimed is:

1. A compound of formula I-b:

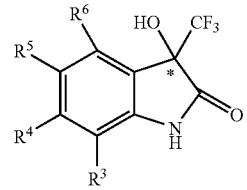

(I-b)

wherein
$R^3$ is t-butyl, 1,1-dimethyipropyl or aryl;
$R^4$ is H;
$R^5$ is $C_{1-6}$-alkyl or $C_{1-6}$-haloalkyl; and
$R^6$ is H, hydroxy or $C_{1-6}$-alkyl;
or an optical isomer or pharmaceutically acceptable salt thereof.

2. The compound of claim 1, which is (R,S)-5,7-Di-tert-butyl-3-hydroxy-3-trifluoromethyl-1,3-dihydro-indol-2-one.

3. A pharmaceutical composition comprising a therapeutically effective amount of a compound of formula I-b,

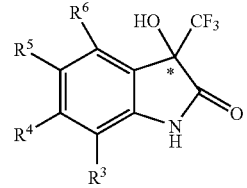

(I-b)

wherein
$R^3$ is t-butyl, 1,1-dimethyipropyl or aryl;
$R^4$ is H;
$R^5$ is $C_{1-6}$-alkyl or $C_{1-6}$-haloalkyl; and
$R^6$ is H, hydroxy or $C^{1-6}$-alkyl;
or an optical isomer or pharmaceutically acceptable salt thereof.

* * * * *

UNITED STATES PATENT AND TRADEMARK OFFICE
CERTIFICATE OF CORRECTION

PATENT NO. : 7,396,853 B2
APPLICATION NO. : 11/492462
DATED : July 8, 2008
INVENTOR(S) : Malherbe et al.

Page 1 of 1

It is certified that error appears in the above-identified patent and that said Letters Patent is hereby corrected as shown below:

- Claim 1, Column 18, line 37: "dimethyipropyl" should read -- dimethylpropyl --.

- Claim 3, Column 18, line 59: "dimethyipropyl" should read -- dimethylpropyl --.

Signed and Sealed this

Twenty-fifth Day of November, 2008

JON W. DUDAS
*Director of the United States Patent and Trademark Office*